United States Patent [19]

Hansen et al.

[11] Patent Number: 4,640,859

[45] Date of Patent: Feb. 3, 1987

[54] INELASTIC, HEAT-ELASTICIZABLE SHEET MATERIAL FOR DIAPERS

[75] Inventors: Paul E. Hansen, Lake Elmo; Susan K. Marquardt, Little Canada, both of Minn.

[73] Assignee: Minnesota Mining and Manufacturing Company, St. Paul, Minn.

[21] Appl. No.: 778,851

[22] Filed: Sep. 23, 1985

Related U.S. Application Data

[62] Division of Ser. No. 565,451, Dec. 27, 1983, Pat. No. 4,552,795.

[51] Int. Cl.$^4$ .................... B32B 5/12; A61F 13/16
[52] U.S. Cl. .................... 428/105; 428/110; 428/118; 428/295; 604/385 A
[58] Field of Search ............ 604/385 A; 428/105, 428/107, 109, 110, 114, 116, 118, 295

[56] References Cited

U.S. PATENT DOCUMENTS

| | | | |
|---|---|---|---|
| 3,245,407 | 4/1966 | Mason | 128/284 |
| 3,369,917 | 2/1972 | Althouse | 2/270 |
| 3,468,748 | 9/1969 | Bassett | 161/122 |
| 3,575,782 | 4/1971 | Hansen | 161/141 |
| 3,694,815 | 10/1972 | Burger | 2/224 |
| 3,912,565 | 10/1975 | Koch et al. | 156/85 |
| 4,136,715 | 6/1979 | McCormack | 138/130 |
| 4,300,562 | 11/1981 | Pieniak | 604/385 A |
| 4,300,967 | 11/1981 | Sigl | 156/164 |
| 4,437,860 | 3/1984 | Sigl | 604/385 A |
| 4,450,026 | 5/1984 | Pieniak | 604/385 A |

FOREIGN PATENT DOCUMENTS 783726  9/1957  United Kingdom .

Primary Examiner—Christopher Henderson
Attorney, Agent, or Firm—Donald M. Sell; James A. Smith; Richard E. Brink

[57] ABSTRACT

Flat, inelastic, dimensionally stable sheet material is formed by stretching parallel elastomeric strands to several times their relaxed length and then bonding them to one or more flat, inelastic webs with inelastic thermoplastic polymer. When the sheet material is heated, the strands contract and the sheet material shirrs. Strips of the flat sheet material can be incorporated in disposable diapers and subsequently shirred to provide elastic waistbands or leg openings.

1 Claim, 5 Drawing Figures

INELASTIC, HEAT-ELASTICIZABLE SHEET MATERIAL FOR DIAPERS

This is a division of application Ser. No. 565,451 filed Dec. 27, 1983, now U.S. Pat. No. 4,552,795.

BACKGROUND OF THE INVENTION

This invention relates to elastic sheet material, a precursor thereof, a method of manufacturing such sheet material, and to products made therewith.

For well over a century, it has been recognized that shirred fabrics could be made by stretching a sheet of rubber, holding it in stretched condition, adhering a fabric to each side, and removing the restraining force to permit the laminate to pucker, or shirr; see, e.g., U.S. Pat. No. 22,038. Similar processes have been practiced since that date; see, e.g., U.S. Pat. Nos. 3,468,748 and 3,575,782, where elastic cords, strings, bands, etc., are handled in much the same way. In more recent times, elastic strips have been incorporated in such products as the cuffs of disposable surgical gowns, the crotch and waistband area of disposable diapers, etc.

The application of elastic strips to a substrate involves the use of specialized machinery and processes to stretch the elastic, attach it in the desired location, and remove the stretching force; see, e.g., U.S. Pat. Nos. 4,239,578, 4,309,236, 4,261,782, and 4,371,417. While technically feasible, these processes do not lend themselves to simple, continuous, trouble-free manufacturing. The elastic, whether in the form of continuous strips, bands, filaments or prefabricated composites, is stretchy and hence difficult to handle. Prior to the present invention, it is believed that no solution has existed for this vexing industrial problem.

BRIEF DESCRIPTION OF THE INVENTION

The present invention provides a product which is flat and flexible, but not elastic, in the form in which it is initially supplied, thus permitting it to be readily utilized in simple and convenient industrial and domestic processes. After attachment to the desired flexible substrate, however, the product of the invention can be readily converted to an elastic state, thereupon providing all the functional advantages of products which are naturally elastic at the time of application.

The present invention thus provides a substantially inelastic, flexible composite flat sheet material, dimensionally stable at room temperature but susceptible of being converted to a shirred elastic condition by exposure to elevated temperatures. This sheet material comprises in combination a plurality of parallel elastomeric strands extended to several times their relaxed length and bonded to at least one substantially inelastic planar web by thermoplastic inelastic polymeric binder. When the composite sheet material is heated for a time and at a temperature such that the stiffness modulus of the composite sheet material is overcome by the contractile force of the elastomeric strands, the strands contract and the sheet material shirrs at right angles to the length of the strands. As used herein the term "dimensionally stable" means that the flat sheet material will contract at most a very slight amount when placed in a tension-free condition. Preferably, the sheet material will contract no more than 5% after two months at room temperature. In any event, however, it will contract no more than 12% when maintained tension free for 10 minutes, greater contraction rendering it difficult to use with simple industrial equipment under normal operating conditions.

While superficially resembling the product of U.S. Pat. No. 3,575,782, the product of the present invention differs significantly. The patent discloses a process of stretching elastic yarns, adhering them to a flexible web with a rubbery latex binder weighing at least as much as the web and evaporating the water from the latex. The patent describes the subsequent exposure to heat to contract the rubber yarns and shirr the fabric; in practice, however, it has been found that even without being heated, the product immediately shirrs as soon as tension is removed and thus never exists in a stable, flat, inelastic, readily handleable form at room temperature. This shirred product, which has enjoyed considerable commercial success, is conventionally wound under substantially no tension into roll form. Upon removal from the roll, the product is cut to desired lengths and widths, in which it is useful as elastic bandages or the like.

One embodiment of the sheet material of the invention is conveniently prepared by a method comprising the steps of a. aligning a plurality of elastomeric strands parallel to each other, b. stretching the strands to at least three times their original length, c. sandwiching the fibers between two flexible webs, at least one of the webs including a substantial quantity of heat-sealable polymer, d. heat sealing the polymer to the strands, e. cooling the composite sheet material to approximately room temperature while holding the elastomeric strands in stretched condition, and f. winding the sheet material into a roll under normal tension.

BRIEF DESCRIPTION OF THE DRAWING

Understanding of the invention will be enhanced by referring to the accompanying drawing, in which like numbers refer to like parts in the several views and in which.

DETAILED DESCRIPTION

Figure 1:
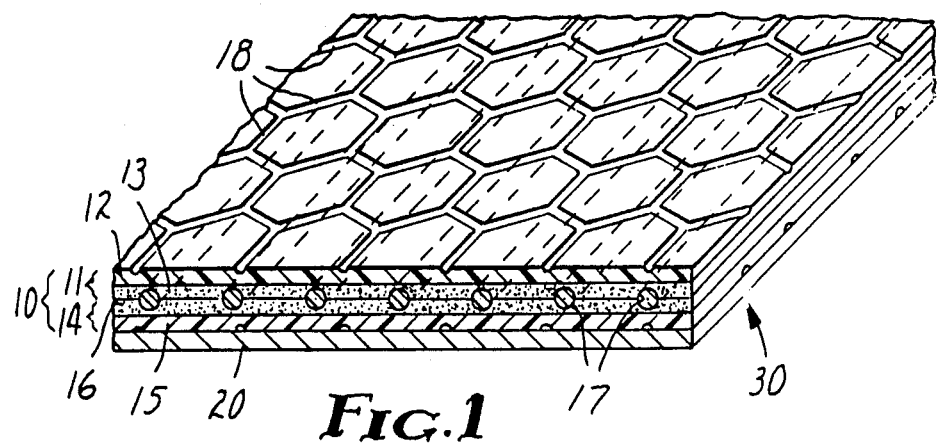
FIG. 1 is a greatly enlarged view of a heat-shrinkable composite sheet material made in accordance with the invention and laminated to a flexible substrate.

In FIG. 1, heat-shrinkable composite 10 comprises a plurality of parallel elastomeric strands, each stretched to several times its relaxed length, sandwiched between first cover web 11 and second cover web 14. Cover web 11 comprises support 12 and heat-sealable binder 13; correspondingly, cover web 14 comprises support 15 and heat-sealable binder 16. (Heat-sealable binders 13 and 16 can be eliminated if supports 12 and 15 are themselves heat-sealable.) Binders 13 and 16 are sealed to each other and to interposed elastomeric strands 17 along heat seal lines 18. The entire heat-shrinkable composite 10 is laminated, (e.g., by sonic bonding, interposition of an adhesive, etc.) to flexible substrate 20, thereby forming laminate 30.

At room temperature, the stiffness of webs 11 and 14 is sufficient to prevent stretched elastomeric strands 17 from returning to their relaxed length. As a result, composite 10 remains in substantially flat condition, even when not subjected to tension, and can be readily handled on conventional assembly lines. After composite 10 is bonded to substrate 20, of course, the ability of elastomeric strand 17 to contract is still further inhibited. When composite 10 or laminate 30 is subjected to a temperature sufficient to render the assembly significantly more flexible, however, the retracting force of strands 17 functions to effect shirring, as is shown in FIG. 2.

Figure 2:
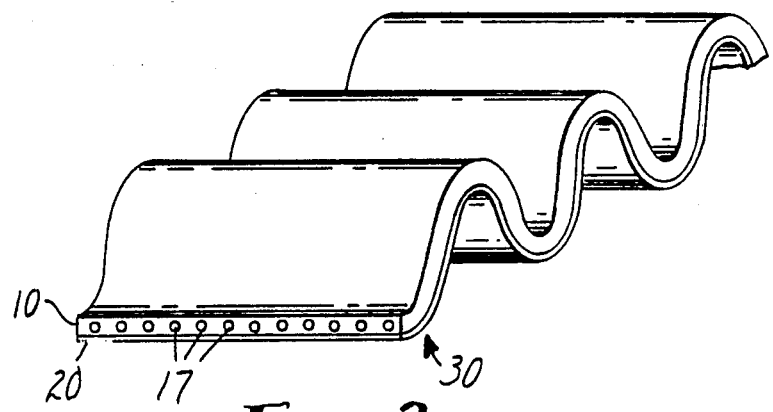
FIG. 2 is a somewhat stylized view of the laminate of FIG. 1 after it has been subjected to an elevated temperature to effect shirring.
Figure 3:
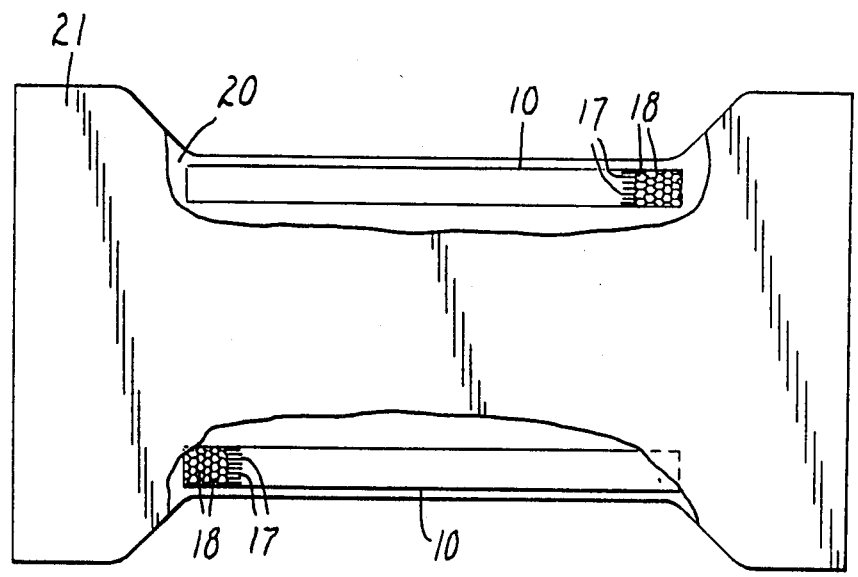
FIG. 3 is a plan view of a disposable diaper embodying the laminated construction of FIG. 1, certain portions of the diaper being broken away to facilitate understanding.
Figure 4:
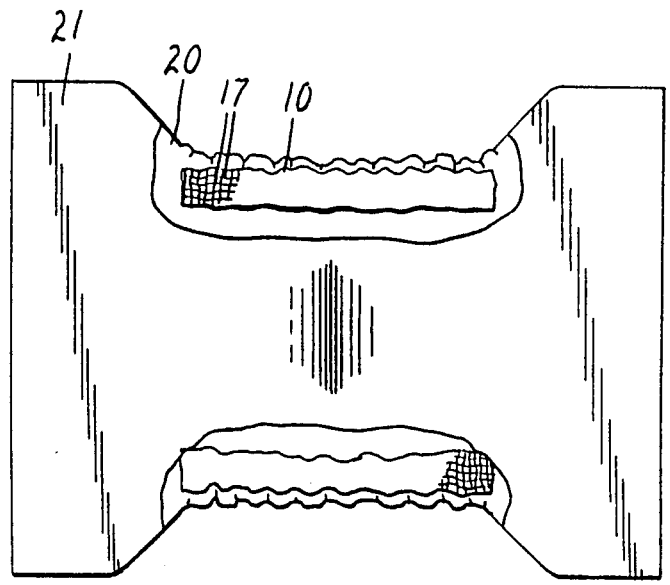
FIG. 4 is a plan view of the diaper of FIG. 3 after shirring has been effected.

FIGS. 3 and 4 correspond, respectively, to FIGS. 1 and 2, substrate 20 in FIGS. 3 and 4 being the outer polyethylene cover of a disposable diaper, the inner aspect being lined with absorbent material (not shown) and protectively covered by moisture-transmitting liner 21. As is shown in FIG. 4, the existence of shirred areas along the sides of the disposable diaper provides an elastic, stretchy area that conforms snugly to the legs of a baby wearing the diaper, greatly reducing the possibility of leakage.

Figure 5:
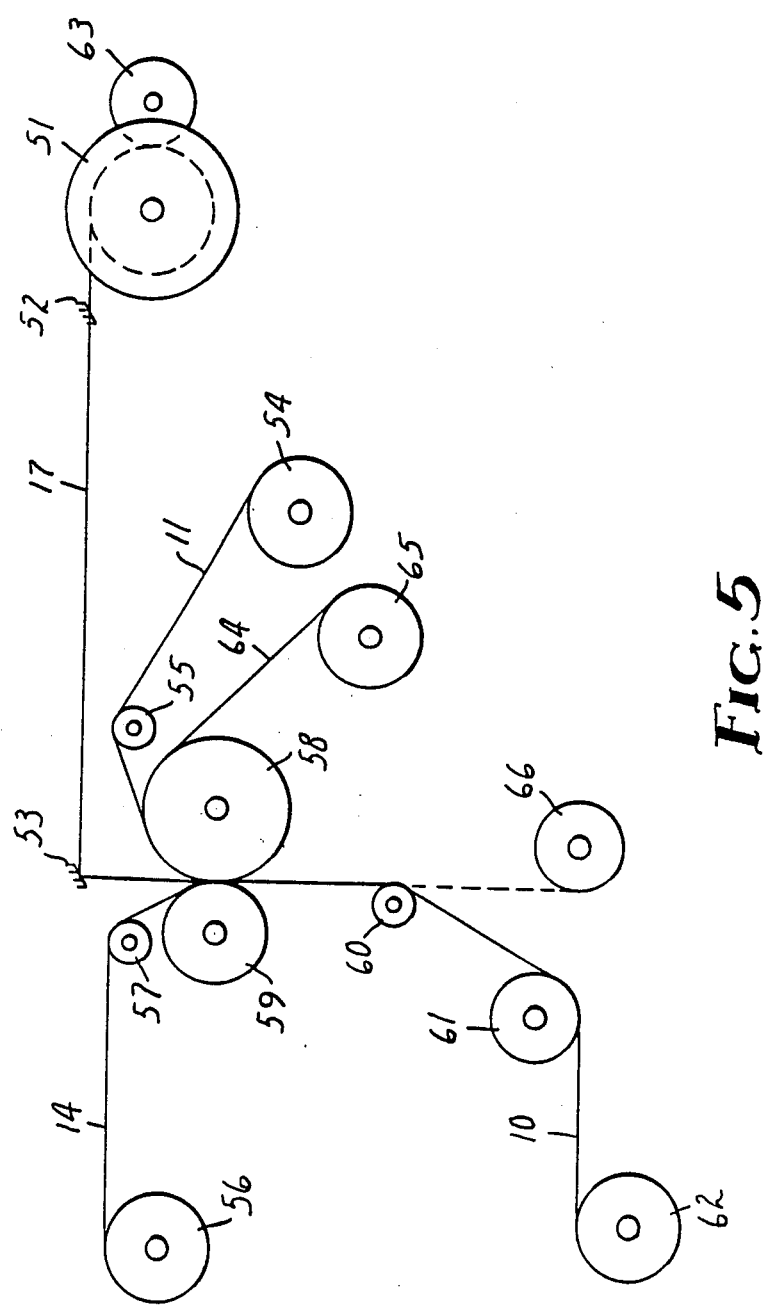
FIG. 5 is a schematic representation of one method of manufacturing the sheet material of FIG. 1.

FIG. 5 shows, in schematic form, a convenient method of manufacturing composite 10. Elastomeric strands 17 are withdrawn from beam 51, passing through combs 52 and 53 to achieve parallel alignment. First thermoplastic cover web 11 is withdrawn from roll 54, passing over support roll 55, while second cover web 14 is withdrawn from roll 56, passing over support roll 57. Strands 17, sandwiched between cover webs 11 and 14, then enter a laminating station consisting of heated embossing roll 58 and rubber roll 59. The amount of heat and pressure applied to the sandwich is that which is sufficient to soften and bond cover webs 11 and 14 to each other and to interposed elastomeric strands 17. Resultant composite 10 then passes around support roll 60 and chill roll 61 and is wound convolutely upon itself on the core of roll 62.

Surface-driven unwind roll 63, operating at a slower surface speed than rolls 58 and 59, controls the rate at which elastomeric strands 17 are withdrawn from beam 51 and thus provides the requisite degree of elongation for strands 17. To prevent adhesion of cover web 11 to embossing roll 58, release liner 64 is unwound from roll 65 and passes around embossing roll 58, preventing cover web 11 from coming in direct contact therewith. Liner 64 is then either wound up with composite 10 onto the core of roll 62 or separated and wound onto the core of roll 66.

The invention will now be described with the aid of an illustrative but nonlimitative example.

Elastomeric strands from a 120-end beam of 360 denier (230-micrometer diameter) spandex fibers, wound under tension with an elongation of 156%, sold by Globe Manufacturing Company under the trade designation "Glospan S-7", were threaded through a series of three combs to obtain a spacing of 10 strands/inch (about 4 strands/cm). As an unwind stand that surface-braked and drove the beam controlled elastomer tension, the elastomeric strands were passed between two 12.7-micrometer films of ethylene:vinyl acetate (EVA) copolymers containing 4-6% vinyl acetate. The two films and elastomeric strands were fed into a laminating station that consisted of a steam-heated embossing roll, having a surface patterned with raised lines defining regular hexagons measuring approximately 1.7 mm on a side, and an 80-durometer rubber support roll. To prevent adhesion of the EVA film to the surface of the embossing roll, a 6.3-micrometer film of biaxially oriented polyethylene terephthalate was interposed between the two. The embossing roll was operated at a surface speed of 7 to 12 fpm (about 2 to 4 meters per minute) so as to provide elastic draw ratios in the range of 3:1 to 5:1. The embossing roll temperature was approximately 125° C., with a nip pressure of 20-30 psi (about 140-210 kPa). Lamination of the webs and strands caused the two films to soften sufficiently to fuse to each other, and to the strands, along lines defining the aforementioned regular hexagonal pattern. The resultant flexible, substantially planar composite was then passed around a chill roll, so as to lower its temperature enough to prevent premature shirring, and wound into roll form.

Subsequent application of heat to the flat composite product resoftens the defined bonded areas of the cover webs, allowing the elastomeric strands to retract and regain their elasticity, simultaneously puckering, or shirring, the entire composite. The temperature used to effect shirring should generally not exceed that at which adhesive failure between the cover webs, or between the cover webs and the strands, will occur. It will, of course, be recognized that time and temperature are interrelated, so that heating at lower temperatures for longer periods of time may result in the same shirring effect obtainable by heating at higher temperature for shorter periods of time. If the flat composite is attached to another flexible substrate (e.g., by stitching, adhesive or sonic bonding, etc.), subsequent heating causes both the composite and the substrate to pucker, in effect imparting a shirred elasticity to the substrate. If the substrate is the wrap of a disposable diaper, such elasticity may be imparted to either the waist band or leg areas. The degree of elasticity in the composite is determined by the original diameter of the elastic strands, the number of strands per unit width, and the original draw ratio of the elastomeric strands before the lamination step. These variables can be altered to provide a product with specific shrinkage and tension characteristics for a desired end use application.

It will be readily appreciated that the foregoing example is merely illustrative, and numerous changes in components and specific procedures can be made without deviation from the spirit of the invention. For example, the cover webs that surround the elastomeric strands in the composite can be two similar films, two different films, a film and a nonwoven web, or two nonwoven webs. The films can include such thermoplastic heat-sealable polymers as ethylene:vinyl acetate copolymers, ethylacrylate:methacrylate copolymers, polyurethanes, ionomers (e.g., "Surlyn"), linear low density polyethylene, and numerous others. These films can be homopolymers, copolymers, blends, coextrusions or multi-layer constructions with polymers that soften at higher temperatures and therefore impart strength and rigidity to the composite. The films can be laminated to themselves or other homopolymeric films (e.g., polyethylene or polypropylene); nonwoven webs made up of polypropylene or polyester fibers; blown microfiber constructions; thermobonded, spunbonded, or spunlaced constructions; or traditional woven or knit fabrics. If, e.g., a film is used as one cover web and a blown microfiber construction as the other, the resultant composite feels soft, and the microfiber surface feels comfortable to the wearer when incorporated into diapers or other items of clothing. Where a single web provides the requisite bond strength and rigidity, the second web may be omitted.

A nonwoven web can be used as a cover web if it contains a heat-sealable fiber component in the form of a binder fiber, a bicomponent fiber, or a fiber blend. Webs including fibers which are a composite of a high-melting polymeric core surrounded by a lower melting polymeric sheath, can also be used. Typical fibers may be 250 micrometers in diameter, with equal weights of a polyethylene terephthalate core and a polyethylene terephthalate:isophthalate sheath. Airlaid nonwoven webs weighing 18–20 g/m², formed of blended composite fibers and polyethylene terephthalate fibers, may be heat-fused in a rolling press to impart structural integrity and then used as cover webs.

Upon lamination, cover webs must bond firmly to each other and to the elastomeric strands; they must also be stiff enough to keep the stretched elastomeric strands from contracting prematurely. In addition, they must soften when heated, to permit the strands to contract and provide for the shirred, elastic composite product. This last-named function will, of course, vary with the thermoplastic polymers and the time/temperature relationship of the heating step. For example, the EVA composite of the foregoing example readily softens when exposed to 110° C. air for about 5 seconds.

The variety of suitable cover webs enables those skilled in the art to prepare composite products having a wide range of unique properties. For example, the use of two porous nonwoven cover webs yields a light weight wrap suitable for holding bandages in place. The use of two thin polyurethane films, one exterior surface being coated with an inert pressure-sensitive adhesive, yields a product suitable for covering cow teats to prevent mastitis during the 3-week "dry" period. Suitable composites may be adhered or stitched to fabric and thereafter heated to create snug-fitting garment cuffs, shirred dress waistbands, etc. Ultra-soft nonwoven webs, colored films, reflective films, semi-permeable membranes, and filter materials could all be used as cover webs to provide products having specific uses.

Similarly, the elastic component need not be limited to spandex strands. Throsted elastomers, in which the exterior of an elastomeric strand (e.g., a 280 denier, or 180-micrometer diameter) is spirally wrapped with a yarn (e.g., a 70 denier, or 84-micrometer diamter, yarn made up of 34 polyester filaments) or nonwoven web, may enhance receptivity of bonding to particular substrates. The elastomeric strands can also be linear block copolymers and the like.

The heat-sealing properties of ethylene:vinyl acetate copolymers make them especially attractive in the practice of the invention, the inclusion of vinyl acetate enhancing processability; although EVA copolymers containing 4–6% vinyl acetate are the least expensive commercially available, higher percentages of vinyl acetate are also useful for specific purposes. For example, copolymers containing 7½% vinyl acetate can be bonded at a temperature about 8° C. lower than those containing 5%. Although somewhat harder to handle, such copolymers are softer, enhancing the drape of composite sheet material in which they are incorporated; they also heat seal more readily to nonwoven webs. Copolymers containing 12% vinyl acetate soften at a still lower temperature and are even softer; these copolymers, however, are rather sticky. Copolymers containing a higher percentage of vinyl acetate are so soft that composite sheet material in which they are incorporated must be carried on a release liner, increasing cost.

The laminating station can employ an oil-heated or electrically-heated hot can, with the surface being either smooth or covered with raised areas defining a variety of embossing patterns. If the surface of the heated roll is smooth, the webs sandwiching the elastomeric strands will be bonded uniformly throughout their length rather than at spaced locations, thereby minimizing the likelihood that any of the strands will be compressed under heat and inadvertently severed. The hardness of the rubber support roll can also be varied to provide the degree or type of bond required for a specific composite.

What is claimed is:

1. A laminate comprising a disposable diaper to which is attached a substantially inelastic, flexible composite flat sheet material that is dimensionally stable at room temperature, said sheet material comprising in combination:

a plurality of parallel elastomeric strands extended to several times their relaxed length and bonded to at least one substantially flat inelastic planar web other than the diaper by thermoplastic, substantially inelastic polymeric binder, the stiffness of the combined web and binder decreasing significantly when heated, thereby permitting the elastomeric strands to contract and the laminate to shirr at right angles to the length of the elastomeric strands.

* * * * *